United States Patent [19]

Cummins, Jr.

[11] Patent Number: 4,462,985

[45] Date of Patent: Jul. 31, 1984

[54] DELIVERY OF BIOLOGICALLY ACTIVE COMPONENTS OF HETEROLOGOUS SPECIES INTERFERON ISOLATES

[75] Inventor: Joseph M. Cummins, Jr., Amarillo, Tex.

[73] Assignee: University of Illinois Foundation, Urbana, Ill.

[21] Appl. No.: 415,525

[22] Filed: Sep. 7, 1982

Related U.S. Application Data

[63] Continuation of Ser. No. 180,464, Aug. 22, 1980, abandoned.

[51] Int. Cl.³ .............................................. A61K 45/02
[52] U.S. Cl. ...................................... 424/85; 438/811
[58] Field of Search ......................................... 424/85

[56] References Cited

U.S. PATENT DOCUMENTS 3,699,222 10/1972 Isaacs et al. ............................ 424/85
4,273,703 6/1981 Osther et al. .......................... 424/85
4,276,282 6/1981 Sugimoto et al. ..................... 424/85

OTHER PUBLICATIONS

Braude, I. et al., Biochem. Biophys. Res. Comm., vol. 89, pp. 612-619, 1979.
Stewart, W., editor, Interferons and Their Actions, CRC Press Inc., Cleveland, Ohio, pp. 49, 59-64, 1977.

Primary Examiner—Blondel Hazel
Attorney, Agent, or Firm—Marshall, O'Toole, Gerstein, Murray & Bicknell

[57] ABSTRACT

Interferon glycoprotein isolates of heterologous species origin are subjected to treatment in a digestive environment and non-species-specific biologically active fractions thereof are administered, preferably through digestive tract tissue, to the circulatory system of mammals, including humans, to secure antiviral, antiproliferative (e.g., antineoplastic) and immunomodulatory (e.g., immunopotentiating) effects ordinarily associated only with parenteral administration of homologous species interferon.

17 Claims, No Drawings

DELIVERY OF BIOLOGICALLY ACTIVE COMPONENTS OF HETEROLOGOUS SPECIES INTERFERON ISOLATES

This is a continuation of application Ser. No. 180,464, filed Aug. 22, 1980, now abandoned.

BACKGROUND

The present invention relates generally to therapeutic uses of interferon and more specifically to treatment of mammals, including humans, with isolates of interferon glycoprotein derived from cells of heterologous mammalian species origin.

"Interferon" is a term generically comprehending a group of vertebrate glycoproteins which are known to exert broad spectrum biological activity—including antiviral, antiproliferative and immunomodulatory activites—in the species of animal from which the substances are derived.

Since the first descriptions of interferon by Isaacs and Lindeman [See, Proc. Roy. Soc. London (Ser. B), Vol. 147, pp. 258 et seq. (1957) and U.S. Pat. No. 3,699,222], the material has been the subject of intensive research on a world-wide basis. Publications abound concerning the synthesis of interferon, its proposed molecular characterization, its clinical applications, and proposed mechanisms of its antitumor, antiviral, and immune system activities. See, generally, such review articles and collections as: DeMaeyer, et al., "Interferons" appearing as Chapter 5 in Comparative Virology, Vol. 15, pp. 205-284, Plenum Press, N.Y., N.Y. (1979); Cantrell, "Why Is Interferon Not In Clinical Use Today" appearing in Interferon 1979, I. Gresser, ed., Vol. 1, pp. 1-28, Academic Press, London (1979); Stewart, "The Interferon System" Springer-Verlag, N.Y., N.Y. (1979); and Dunnick, et al., "Clinical Trials with Exogenous Interferon", J. Infect. Diseases, 139, No. 1, pp. 109-123 (1979).

Owing to the disparate origins of the research contributing to the sum of the knowledge in the art concerning interferon, its characteristics and its uses, there exists a substantial lack of uniformity in such matters as classification of interferon types. There are also numerous, sometimes contradictory, theories concerning the mode of action of interferon in producing clinical effects. The following brief summary is believed to provide a fair analysis of background information such as needed for understanding the present invention.

A. Origins, Nomenclature and Physical Characteristics of Interferon

Although originally isolated from cells of avian origin (chick allantoic cells), interferon production has been observed in cells of all classes of vertebrates, including mammals, amphibians, reptiles, etc. Interferon production by vertebrate cells is seldom spontaneous but is often readily "induced" by treatment of cells (in vivo or in vitro) with a variety of substances including viruses, nucleic acids (including those of viral origin as well as synthetic polynucleotides), lipopolysaccharides and various antigens and mitogens.

Interferon is generally named in terms of correlation to the species of animal cells producing the substance (e.g., human, murine, bovine, etc.) as well as to the type of cell involved (e.g., leukocyte, lymphoblastoid, fibroblast) and, occasionally, the type of inducer material responsible for interferon production (e.g., virus, immune). Currently, interferon is loosely classified by some researchers according to induction mode as either Type I or Type II, with the former classification comprehending viral and nucleic acid induced interferon and the latter class including the material produced as a lymphokine through induction by antigens and mitogens. Various forms of interferon are distinguished by size, antigenicity, degree of glycosation and pH stability.

Determination of precise molecular structures for interferon glycoprotein is presently beyond the capacities of the art. In the years since interferon was first characterized as proteinaceous on grounds of its inactivation by trypsin, attempts to purify and uniquely characterize it have been frustrated by its high specific activity as well as its apparent heterogeneity, even in samples derived from a single cell type and using a single specific inducer. As one example, Thang, et al., P.N.A.S., Vol. 76, No. 8, pp. 3717-3721 (1979) report that samples of human leukocyte interferon produced by challenge of leukocytes with Sendai virus can be separated into at least "two classes of subspecies" by agarose-polynucleotide affinity chromatography with the two, in turn, displaying differing degrees of antiviral activity.

Interferon of human and murine origin is quantified by specific antiviral activity in terms International Units ("IU"), this despite knowledge that, e.g., the molecular weight of human leukocyte and lymphoblastoid interferon ranges between 13,000 to 25,000 daltons.

B. Biological Activities of Interferon

In its earliest applications, interferon was employed exclusively as an antiviral agent and the most successful clinical therapeutic applications to date have been in the treatment of viral or virus-related disease states. It became apparent, however, that exogenous interferon was sometimes capable of effecting regression or remission of various metastatic diseases. A summary of clinical trials of interferon as an antiviral and antiproliferative therapeutic agent through late 1978 is contained in Dunnick, et al. supra.

The clinical agent of choice in this work has been human leukocyte interferon, "mass-produced" by procedures involving collection and purification of vast quantities of human buffy coat leukocytes, induction with virus and isolation from culture media. The need for interferon of human source is, of course, consistent with the long-standing conclusion that interferon is "species specific", i.e., biologically active, in vivo, only in species homologous to the source cells.

Interferon is administered parenterally, i.e., intramuscularly and intradermally, with some successful topical usages having been reported. It is seldom administered intravenously owing to substantial adverse effects attributable to "contaminants" in crude and even highly purified isolates. Parenthetically, while providing interferon dosages in the range of 1 to $5 \times 10^6$ IU, interferon isolates employed in clinical studies actually contain less than about 0.1 percent interferon glycoprotein—the balance of the preparations comprising extraneous materials such as cellular debris, viral fragments and the like. To date, there have been no reports of therapeutically successful oral administration of interferon. This is consistent with the belief, widely held, that the glycoprotein will not withstand exposure to a digestive environment, such as found in mammalian therapy candidates. It is simply not expected that the biological activity of the glycoprotein could be retained after the molecules are subjected to the degradative effects of carbohydrases (e.g., amylase in saliva), or simple esterases, or the proteolytic hydrolytic enzymes in gastrointestinal secretions (e.g., trypsin, pepsin, chymotrypsin, carboxy peptidases A and B) and in cells of the intestinal mucosa (e.g., the aminopeptidases). These beliefs as to lack of oral efficacy are supported in large part by the prevailing understanding in the art that, while the digestive environment may not be hostile to all proteinaceous materials (proteolytic enzymes themselves being proteins), proteins are generally not transported across the gastrointestinal membrane. Thus, were interferon glycoproteins able to withstand a digestive environment, they would not be expected to be made available to the circulatory system by absorption through digestive tract tissue.

Exceptions to the "rule" concerning intact absorption of macromolecular proteinaceous materials are few. See, e.g., Wiseman, "Absorption from the Intestine", pp. 65-67, Academic Press, N.Y., N.Y. (1964); Bockman, et al., *Anat. Res.*, Vol. 155, 603-622 (1966); Walker, et al., *Gastroenterology*, Vol. 67, 531-550 (1974); Warshaw, et al., *Gastroenterology*, Vol. 66, pp. 987-992 (1974); Freeman, et al., *Ann.Rev.Med.*, Vol. 29, pp. 99-116 (1978); U.S. Pat. No. 3,004,893 and U.S. Pat. No. 4,132,776. In general, the most substantial exception involves absorption of macromolecules by digestive tissue of neonatal animals prior to maturation of intestinal epithelial cell membranes. Indeed, the single known suggestion in the art that interferon might be orally effective involved studies with neonatal mice [Schafer, et al., *Science*, Vol. 176 pp. 1326-7 (1972)].

In addition to use in antiviral and antitumor therapy, interferon has rather recently been noted to possess immunomodulatory effects, both immunopotentiating and immunosuppressive in nature. See, e.g., Sonnenfeld, et al., "A Regulatory Role For Interferon In Immunity", Annals, N.Y. Acad. Sci., Vol. 322, pp. 345-355 (1979). While no human clinical or in vivo animal work specifically directed to evaluation of immunological effects of interferon has been reported, it is proposed by some that the antitumor effects of interferon are at least in part related to immune stimulation or activation of so-called "natural killer cells," macrophages and T-lymphocytes. See, e.g., Kershner, "New Directions in Cancer Chemotherapy" *A.S.M. News*, Vol. 46, No. 3, pp. 102 et. seq. (1980).

Finally, "new" biological activities for exogenous interferon are consistently being ascertained. Cantrell, et al., *New Eng. Jour. Med.*, Vol. 302, No. 18, p.1032 (1980) report an effect of interferon in transiently diminishing high density lipoprotein levels and total cholesterol values, suggesting that interferon in humans, may influence cardiovascular disease.

The absence of widespread clinical usage of interferon at the present time is attributable to a number of factors, but principally the shortness of supply of the material showing greatest clinical promise, i.e., human leukocyte interferon. It has been estimated that in Finland—the country supporting the largest production of interferon—enough of the substance is prepared annually to treat either 10,000 cases of herpes keratitis or 200 case of chronic neoplastic disease.

The scarcity of human leukocytic interferon for clinical applications has prompted many researchers to reexamine the species specificity phenomenon in greater depth with the hope that some means might be found to chemically modify the much more readily available supplies of non-human interferon for use in humans. Generally at the forefront of these researchers is W. A. Carter. [See, e.g., "Minireview Glycosylation; Intraspecies Molecular Heterogeneity and Trans-Species Activity of Mammalian Interferon", *Life Sciences*, Vol. 25, pp. 717-28, Pergamon Press (1979); "Bypassing the 'Species Barrier' With Carbohydrate-Altered Interferon From Leukocytes", *Cancer Research*, Vol. 39, pp. 3790-3795 (1979); and Carter, et al., *Molecular Pharmacology*, Vol. 15, pp. 685-690 (1979).] Carter has exhaustively reviewed the art teachings with respect to in vitro activities of interferon in protecting cells of heterologous species from infection by virus and proposes an integrative model wherein the ability of interferon glycoprotein to cross or not cross species lines lies in the carbohydrate moiety and the cross-species biological activity is the function of the polypeptide portion. See also, Braude, et al., "Differential Inactivation and Separation of Homologous and Heterologous Antiviral Activity of Human Leukocyte Interferon By A Proteolytic Enzyme", *Biochem. Biophys. Res. Comm.*, Vol. 89, No. 2, pp. 612-619 (1979) and Thang, et al., supra. To date, however, there have been no reports of the successful use of heterologous species interferon in vivo to develop those antiviral, antiproliferative or immunomodulatory effects ordinarily associated with administration of homolgous species interferon.

In sum, interferon glycoprotein is presently recognized in the art as possessing enormous therapeutic potential. Interferon is as yet incompletely characterized as to biologically active components and precise mode of action. Species specificity characteristics impose severe limits on the range of its therapeutic utilities and concurrently severely restrict availability of interferon for clinical application.

SUMMARY

According to the present invention, mammals, including humans, are treated with therapeutically effective amounts of interferon glycoprotein isolated from cells of heterologous mammalian species origin. More specifically, antiviral, antiproliferative and/or immunomodulatory effects heretofore ordinarily obtained only upon parenteral administration of isolates of homologous species interferon are obtainable through administration of more readily available isolates of interferon glycoprotein having heterologous mammalian species origins. Heterologous species interferon preparations are first subjected to a digestive environment wherein non-species-specific biologically active fractions thereof are substantially freed from extraneous polypeptides and/or carbohydrates with which the biologically active fractions are ordinarily associated. The active components are administered to the circulatory system of the recipient animal, preferably through digestive tract tissue.

In the most preferred procedures of the invention, heterologous species interferon is administered to the alimentary canal of the recipient mammal, whereby the digestive materials in the canal operate on the isolate. Within such a digestive environment, extraneous carbohydrate and/or polypeptide materials which are not essential to the activity of biologically active fractions of interferon (but which are normally associated therewith when isolated) are degraded without detectable inactivation of the biologically active fractions. Such active fractions are thereafter absorbed through digestive tract tissues and enter the circulatory system of the recipient. Alternatively, the heterologous species interferon isolate may be treated in vitro under conditions substantially duplicating the digestive environment of the recipient mammal and thereafter administered to the mammal, either orally or, after suitable isolative procedures, parenterally.

Mammals treatable according to the invention and suitable as cell sources for interferon production include those of the human, feline, bovine, equine, laprine and porcine species. The preferred types of interferon for use in the invention include fibroblast interferon as well as immune type interferon. Presently preferred practices of the invention include oral administration of bovine fibroblast and/or immune type interferon to human patients suffering from neoplastic and/or viral diseases, including, e.g., malignant melanomas and benign papillomas of probable viral origin.

Further aspects and advantages of the invention will become apparent upon consideration of the following detailed description including the illustrative examples.

DETAILED DESCRIPTION

As employed herein, "interferon" and "interferon glycoprotein" shall be synonymous and shall have the meaning ordinarily attributed thereto in the art, including, but not limited to the meaning ascribed thereto in U.S. Pat. No. 3,699,222.

The term "isolated from cells of heterologous mammalian species origin" as applied to interferon shall designate derivation not only from in vitro mammalian cell growth media and in vivo mammalian cellular exudates or secretions, but also from other suitable cellular sources. As such, the term is intended to designate interferon such as may be obtained as an in vitro isolate from media supporting growth of non-mammalian cells which have been the object of genetic transformation involving mammalian DNA. "Isolate" shall comprehend preparations resulting from attempted purification of interferon present in cell growth media, cell exudates and cell secretions, with no specific limitation as to precise concentration of interferon.

"Digestive environment" shall mean and include conditions substantially duplicating those commonly present within the digestive tract of a recipient mammal, including, but not limited to, pH and temperature conditions and the presence of one or more hydrolytic, phosphorylytic, oxidation-reduction, transferring, decarboxylating, hydrating or isomerizing enzymes.

As employed herein, "alimentary canal" and "digestive tract" shall be essentially synonymous and shall mean and include that anatomical portion of a mammal, e.g., the mouth, pharynx, stomach, duodenum, jejunum, ileum and large intestine in humans, wherein digestive processes occur. "Parenteral administration" shall mean and include administration to a mammal by means other than introduction into the alimentary canal. "Circulatory system" shall mean and include the hematic and/or lymphatic system of a mammal.

The following examples serve to illustrate practice of the invention wherein an interferon glycoprotein isolate from cells of heterologous mammalian species origin is delivered to the circulatory system by administration to the alimentary canal of a recipient animal, whereby the isolate is subjected to a digestive environment in the recipient prior to the absorption of biologically active fractions thereof through alimentary canal wall tissues.

EXAMPLE 1

Bovine fibroblast interferon was prepared as follows:

Primary bovine fetal kidney (BFK) or bovine testicular (BT) cells were grown to confluency in cell culture. Stocks of bluetongue virus (international serotype 10) were prepared in baby hamster kidney (BHK) cells or VERO cells and had titers of $10^6$ to $10^8$ PFU/ml. The BFK or BT cells were challenged with bluetongue virus (multiplicity of infection of greater than 1 was best) and supernatant fluids were harvested when the cytopathic effect (CPE) involved the entire cell sheet, i.e., about 24 hours. The supernatant fluids were dialyzed for 24 hours in a KCl-HCl buffer (pH 2.0) and 24 hours in a phosphate buffered saline (pH 7.4) before ultracentrifugation at 100,000×g for 60 minutes. The interferon activity (expressed as "units" as opposed to IU) was assayed by a plaque reduction method using vesicular stomatitis virus (VSV) as a challenge virus on BFK cells (Rosenquist and Loan, "Interferon Production With Strain SF-4 of Parainfluenza-3 Virus" *Am. J. Vet. Res.*, 28, pp. 619–628 (1967)].

EXAMPLE 2

Bovine nasal secretion interferon was prepared as follows:

Calves were inoculated intranasally with a vaccinal strain of infectious bovine rhinotracheitis (IBR) virus and the nasal secretions were collected by tampon for 2–8 days after virus inoculation. [McKercher, et al., "A Simple Method For Obtaining Undiluted Nasal Secretions From Cattle," *Am. J. Vet. Res.*, 34, pp. 837–838 (1973); Cummins, et al., "Protection of Calves Against Rhinovirus Infection by Nasal Secretions Interferon Induced by Infectious Bovine Rhinotracheitis Virus," *Am. J. Vet. Res.*, 41, pp. 161–165 (1980); Todd, et al., *Infect. Immun.* 5, pp. 699–706 (1972)]. Nasal secretions were subjected to dialyzation and ultracentrifugation as described in Example 1.

EXAMPLE 3

This example illustrates therapeutic effectiveness of orally administered heterologous species interferon in treatment of benign papillomas of probable viral origin in human patients.

A. A male patient having a wart which was three millimeters in diameter and which had been present for about ten years consumed 30,000 units of bovine interferon prepared according to Example 2. The single dose was incorporated in about 10 ml of tissue culture medium. The wart was completely resolved within three weeks after treatment and did not recur.

B. A female patient complaining of two plantar warts and xanthalasma of several years duration was given an initial oral dose of bovine interferon of Example 1 totaling 10,000 units in nine equal portions on a twice-daily schedule. After about three weeks, the plantar warts were substantially reduced in size. Approximately eight weeks after the first dose, about 2500 units of interferon of Example 2 was orally administered in four equal doses, twice daily. Within a week, the warts exhibited a vascular response and had a reddened appearance. Approximately 12 weeks after commencement of treatment, a single oral dose of 5250 units of interferon of Example 2 was given, followed one week later with 21,000 units of Example 1 interferon, orally administered in ten, twice-daily doses. Within three weeks thereafter, the plantar warts were somewhat painful upon application of pressure and "drier" as well as further reduced in size. No more interferon was given and no further improvements in the warts were noted.

The xanthalasma, which had been unchanged for two years, flattened and was reduced in size within a week after the first dose of interferon. The xanthalasma reappeared but partially regressed again after the second dose of interferon. The xanthalasma reappeared and has remained essentially unchanged since administration of the third dose.

C. A male patient with a plantar wart was given a single, 8600 units, oral dose of Example 2 interferon. Within three weeks, there appeared to be an increase in blood supply to the wart and a size reduction of about one-half. No further treatments were given nor were further improvements noted.

EXAMPLE 4

This Example relates to the therapeutic effectiveness of orally administered heterologous species interferon in treatment of malignant melanoma in human patients.

A. A first female patient had experienced a two year history of malignant melanoma on the leg. Prior treatments included surgery (at about three months after diagnosis) which revealed metastases to the inguinal lymph nodes. Chemotherapy for one year after surgery proved ineffective, as did Laetrile treatments commencing five months prior to interferon therapy. At commencement of interferon therapy, approximately forty tumors were visible on the leg. With Laetrile therapy continuing, the patient was given a total oral dose of 110,000 units of bovine interferon of Example 2 on the following dosage regimen Week 1—6600 units
Week 3—27,000 units
Week 4—36,600 units
Week 5—39,300 units Within four months after initiation of treatment, all but one of the tumors had disappeared and the single remaining tumor regressed completely by eight months after treatment began. As of 22 months after therapy commencement, there were no recurrences of tumors or indications of side effects from interferon therapy.

B. A second female patient had experienced a two-year history of malignant melanoma on the leg with prior treatments including two surgical procedures. Amputation of the lower leg was refused. Laetrile treatments were begun but had not prevented tumors from increasing in number and size. Interferon therapy was commenced according to the following oral dosage schedule.

| Week | Type | No. Doses | Total Amount |
|---|---|---|---|
| 1 | Example 1 | 21 (Bid) | 8400 units |
| 3 | Example 1 | 21 (BID) | 5900 units |
| 5 | Example 2 | 15 (BID) | 3000 units |
| 7 | Example 1 | 15 (BID) | 3000 units |
| 11 | Example 1 | 15 (BID) | 15,400 units |
| 13 | Example 1 | 19 (BID) | 11,900 units |
| 16 | Example 2 | 9 (TID) | 25,400 units |
| 19 | Example 2 | 17 (BID) | 40,000 units |
| 22 | Example 2 | 16 (BID) | 320,000 units |

Approximately 113,000 units was orally administered up through the 22nd week and the total treatment dosage was 433,000 units. Within one week of commencement of treatment the tumors were noticeably drier and required fewer changes of dressings. Seepage and oozing from the leg has nearly ceased. Over the following weeks the large tumors lost volume and flattened and some of the smaller tumors regressed in size. Leg pain greatly subsided. No new tumors have developed during therapy and the largest of tumors appeared to be undergoing vascular changes. The patient complains of a "burning" sensation in her leg which is completely relieved during interferon treatment by returns upon completion of interferon dosages.

EXAMPLE 5

This Example relates to oral administration of bovine interferon to a human patient terminally ill with metastatic breast cancer. A total of 8400 units of interferon of Example 1 was administered in 21 equal doses BID. The patient suffering from metastases to the brain and bone, expired two weeks after treatment was commenced.

EXAMPLE 6

This example relates to the therapeutic effectiveness of orally administered heterologous species interferon in the treatment of feline leukemia. A kitten showing clinical signs of chronic oral ulcers, non-regenerative anemia, enlarged lymph nodes, lymphocytosis, and a positive feline leukemia virus test (Leukassay from Pitman-Moore) was treated with $1.7 \times 10^6$ units of bovine fibroblast interferon (per Example 1) orally. The oral ulcers have healed, the anemia has resolved, the lymph nodes appear normal, and the amount of feline leukemia viral antigen in the blood had declined (as measured by performing the Leukassay on serial dilutions of blood). The lymphocytosis has, however, continued.

Another cat displaying clinical signs of anorexia, depression, vomiting, and weight loss for about 6 weeks was found to be feline leukemia virus positive (Leukassay). A littermate had died of feline leukemia 2 months before. After treatment with $1 \times 10^6$ units of bovine interferon (per Example 1) orally, the cat was clinically normal except the weight gain has not yet replaced the weight loss. The amount of feline leukemia viral antigen in the blood has not declined in 3 weeks.

A third cat with a leukocytosis, and anemia, severe depression, and positive for feline leukemia virus (Leukassay) was treated for five days with a total of $5 \times 10^5$ units of bovine interferon of Example 1. Prednisolone was also administered. Within ten days after treatment the cat appeared clinically normal, the white blood cell count returned to normal and the hematocrit improved from 12 to 18.

EXAMPLE 7

Three hamsters, four guinea pigs, and eight mice have been treated orally with varying amounts of bovine interferon of Example 1. No clinical illness occurred during treatment, no weight loss was noted, and no signs of toxicity attributable to interferon were seen histopathologically after one week's therapy. Total dosages have ranged up to 400,000 units of interferon per kg of body weight.

While the foregoing illustrative examples describe use of bovine interferon, and while bovine interferon is preferred on grounds of its easy availability in relatively large quantity, it will be recognized that mammals may be effectively treated with heterologous species interferon of procine, equine, laprine, feline and human sources. Cross species in vitro antiviral activity of varying degree is described for the bovine, porcine, equine, laprine, feline and human species. [See Tovey et al., J.

Gen. Virol. 36, pp. 341–344 (1977); Carter, Life Sciences 25, pp. 717–728 (1979); Babiuk and Rouse, Intervirology, 8, pp. 250–256 (1977); Desmyter and Stewart, Virology, 70, pp. 451–458 (1976); Stewart, The Interferon Systems, Springer Verlag, N.Y., N.Y., pp. 135–145 (1979).] Those species of interferon which show some cross species antiviral protection may share a common sequence of amino acids which, when freed from association in the entire interferon molecule, exhibit similar antitumor activity.

While phosphate buffered saline or Eagles' Minimal Essential Medium was used as a carrier for interferon in the above Examples, other pharmaceutically acceptable diluents adjuvants and carriers such as are commonly employed in oral and parenteral therapy may be employed.

While above Examples relate to therapeutic usage in humans and cats, horses, cattle, and rabbits are treatable in a similar manner.

Dosage required for therapeutic effect are expected to vary widely depending on the mammal patient and condition treated, with from about 10 to about 1,000 units per kg in unit dosage form is believed operative.

According to another aspect of the invention, a specific heterologous species interferon isolate may be efficaciously pretreated under digestive conditions and administered to the recipient animal's circulatory system. Such practice involves "pre-digesting" the isolate in vitro in a suitable digestive environment comprising, e.g., a strongly acidic solution of pepsin and/or solutions or suspensions of the various enzymatic substances operative in digestive processes. If the digestive environment substantially duplicates that of a proposed recipient animal, the entire combination of reagents, reactants, and products may be administered to the alimentary canal of the recipient to effect delivery of the biologically active component of the isolate to the circulatory system. Alternatively, the resultant "digested" isolate containing the active fracion may be reclaimed, i.e., separated as smaller molecular weight components from the digestive environment (e.g. by dialysis, centrifugation and chromatography), and administered orally or parenterally. In either event, the active component will be suitably rapidly incorporated into the recipient animal's circulatory system in a manner essentially eliminating the risks of adverse reaction which ordinarily accompany the administration of "foreign," undergraded polypeptides.

Upon consideration of the foregoing description and illustrative examples, numerous modifications and variations in the practice of the invention are expected to occur to those skilled in the art.

What is claimed is:

1. In the method for enhancing the competence of a non-human mammal's response to viral and neoplastic disease states wherein exogenous interferon is provided to the circulatory system of a mammal in need of such enhancement, the improvement comprising:
administering to the alimentary canal of the recipient mammal an effective amount of interferon isolated from cells of heterologous mammalian species origin, whereby said interferon is subjected to a digestive environment in the recipient mammal's digestive tract and the non-species-specific antiviral or antineoplastic fraction of said interferon is absorbed through digestive tract tissue and transported to the recipient mammal's circulatory system.

2. The improvement of claim 1 wherein the quantity of interferon administered to the alimentary canal comprises, in unit dosage form, from about 10 to about 1,000 units per kg of body weight in combination with a pharmaceutically acceptable diluent, adjuvant or carrier.

3. The improvement of claim 1 wherein said interferon isolated from cells of heterologous species origin is isolated from cells of human, feline, bovine, equine, laprine or procine species origin.

4. The improvement of claim 1 wherein the recipient mammal is of the feline, bovine, equine, laprine or procine species.

5. The improvement of claim 1 wherein said interferon isolated from cells of heterologous species origin is isolated from cells of bovine species origin, the recipient animal is of the feline species and the response to be enhanced is a response to a feline leukemia disease state.

6. In the method for enhancing the competence of a human's response to a viral disease state wherein exogenous interferon is provided to the circulatory system of a human in need of such enhancement, the improvement comprising:
administering to the alimentary canal of the recipient an effective amount of interferon isolated from cells of heterologous mammalian species origin, whereby said interferon is subjected to a digestive environment in the recipient's digestive tract and the non-species-specific antiviral fraction of said interferon is absorbed through digestive tract tissue and transported to the recipient's circulatory system.

7. The improvement of claim 6 wherein the quantity of interferon administered to the alimentary canal comprises, in unit dosage form, from about 10 to about 1,000 units per kg of body weight in combination with a pharmaceutically acceptable diluent, adjuvant or carrier.

8. The improvement of claim 6 wherein said interferon isolated from cells of heterologous species origin is isolated from cells of feline, bovine, equine, laprine or procine species origin.

9. The improvement of claim 6 wherein said interferon isolated from cells of heterologous species origin is isolated from cells of bovine species origin.

10. The improvement of claim 9 wherein said interferon is fibroblast interferon.

11. The improvement of claim 9 wherein the response to be enhanced is a response to a benign papilloma disease state.

12. In the method for enhancing the competence of a human's response to a neoplastic disease state wherein exogenous interferon is provided to the circulatory system of a human in need of such enhancement, the improvement comprising:
administering to the alimentary canal of the recipient an effective amount of interferon isolated from cells of heterologous mammalian species origin, whereby said interferon is subjected to a digestive environment in the recipient's digestive tract and the non-species-specific antineoplastic fraction of said interferon is absorbed through digestive tract tissue and transported to the recipient's circulatory system.

13. The improvement of claim 12 wherein the quantity of interferon administered to the alimentary canal comprises, in unit dosage form, from about 10 to about 1,000 units per kg of body weight in combination with a pharmaceutically acceptable diluent, adjuvant or carrier.

14. The improvement of claim 12 wherein said interferon isolated from cells of heterologous species origin is isolated from cells of feline, bovine, equine, laprine or procine species origin.

15. The improvement of claim 12 wherein said interferon isolated from cells of heterologous species origin is isolated from cells of bovine species origin.

16. The improvement of claim 15 wherein said interferon is fibroblast interferon.

17. The improvement of claim 15 wherein the response to be enhanced is a response to a malignant melanoma disease state.

* * * * *